United States Patent [19]

Cichowski et al.

[11] 4,086,290

[45] Apr. 25, 1978

[54] OXIDATIVE DEHYDROGENATION PROCESS

[75] Inventors: Robert S. Cichowski, San Luis Obispo, Calif.; Floyd E. Farha, Jr., Bartlesville, Okla.

[73] Assignee: Phillips Petroleum Company, Bartlesville, Okla.

[21] Appl. No.: 699,729

[22] Filed: Jun. 24, 1976

Related U.S. Application Data

[62] Division of Ser. No. 542,006, Jan. 17, 1975, Pat. No. 3,993,591, which is a division of Ser. No. 264,932, Jun. 21, 1972, Pat. No. 3,870,764.

[51] Int. Cl.² .............................................. C07C 11/12
[52] U.S. Cl. ............................. 260/680 E; 260/666 R; 260/668 D; 260/683.3
[58] Field of Search ........... 260/680 S, 666 R, 668 D, 260/683.3

[56] References Cited

U.S. PATENT DOCUMENTS

| 3,409,697 | 11/1968 | Callahan et al. ................. 260/680 E |
| 3,642,930 | 2/1972 | Grasseli et al. ................. 260/680 E |
| 3,660,513 | 5/1972 | Davison ........................... 260/680 E |
| 3,790,500 | 2/1974 | Walker ............................. 260/680 E |
| 3,810,953 | 5/1974 | Cichowski et al. .............. 260/680 E |
| 3,851,009 | 11/1974 | Cichowski ....................... 260/680 E |
| 3,852,369 | 12/1974 | Walker et al. ................... 260/680 E |
| 3,862,255 | 1/1975 | Bertus et al. .................... 260/680 E |
| 3,862,910 | 1/1975 | Cichowski ....................... 260/680 E |
| 3,870,764 | 3/1975 | Cichowski et al. .............. 260/680 G |
| 3,993,591 | 11/1976 | Cichowski et al. .............. 260/680 G |

FOREIGN PATENT DOCUMENTS

| 1,331,277 | 4/1962 | France ............................. 423/680 E |

*Primary Examiner*—O. R. Vertiz
*Assistant Examiner*—Eugene T. Wheelock

[57] ABSTRACT

Compositions comprising Fe/P/Group IIIA components are effective as catalysts in processes to convert organic compounds to compounds having a greater degree of unsaturation.

27 Claims, No Drawings

OXIDATIVE DEHYDROGENATION PROCESS

This application is a divisional application of U.S. application Ser. No. 542,006, filed Jan. 17, 1975, now U.S. Pat. No. 3,993,591, Nov. 23, 1976, which is a divisional of Application Ser. No. 264,932, filed June 21, 1972, now U.S. Pat. No. 3,870,764, March 11, 1975.

FIELD OF THE INVENTION

The invention relates to compositions found effective as dehydrogenation catalysts. The invention further relates to dehydrogenation processes utilizing the compositions as catalysts.

BACKGROUND OF THE INVENTION

A variety of compositions useful for employment as catalysts in dehydrogenation processes are known. However, the search for better, more effective, catalyst compositions, preparations, and processes of utilization continues.

OBJECTS OF THE INVENTION

It is an object of our invention to provide novel compositions useful as catalysts. It is a further object of our invention to provide effective yields of desired products through dehydrogenation processes.

Other aspects, objects, and several advantages of our invention will become apparent to those skilled in the arts to which our invention most nearly appertains upon consideration of our disclosure as presented in this specification further including the appended claims.

SUMMARY OF THE INVENTION

According to our invention, novel compositions are provided which comprise Fe/P promoted with a Group IIIA metal component. One or more of the elements in the composition can be combined with oxygen.

These compositions, employed as catalysts, exhibit effective properties and abilities to convert, for example, a paraffin to an olefin, such as a butane to butene, or to convert a monoolefin to a diene, such as an isoamylene to isoprene or a butene to butadiene. These and other dehydrogenation conversions are valuable processes for the conversion of organic materials into other, frequently less plentiful or available and therefore more valuable, organic compounds.

DETAILED DESCRIPTION OF THE INVENTION COMPOSITIONS

The compositions of our invention comprise (I) an iron component, (II) a phosphorus component, promoted by (III) a Group IIIA component, more particularly one or more of boron, aluminum, gallium, indium, or thallium. One or more of such components can be combined with oxygen in the compositions. A presently preferred preparation is by calcining an admixture of the component-containing compounds in a molecular oxygen-containing atmosphere.

In our compositions as catalysts according to one aspect of our invention, the relative amounts of each component can vary widely, so long as there is an effective relationship in the final composition produced, i.e., each component is present in a sufficient weight relationship of one to the other so as to provide catalytic effectiveness of the composition combination.

Of course, any particular composition component need not necessarily be present in the elemental state, but can be present in a combined form with one or more other elements. Neither the valence state nor the elemental state, combined or uncombined state, is considered critical in our invention, and the exact nature as to combined or uncombined form, oxidative or reduced state, of any particular component or constituents in the compositions of our invention, is not to be limitative of our invention, since it is not at present possible to particularly define the exact chemical state of any particular component.

Presently preferred for most catalytic purposes are compositions in which iron represents about 15 to 45 weight percent, phosphorus about 15 to 40 weight percent, and Group IIIA metal about 0.1 to 10 weight percent, of the total composition. The total percent values of I plus II plus III need not total 100. Oxygen can be present in a combined form with one or more other components sufficient to satisfy the unsatisfied valences thereof. Each component of our compositions is calculated as the element itself.

Two or more Group IIIA metal components can be utilized for our compositions, and where such are employed, the total thereof is that reflected in the group component weight relationships expressed.

It presently is preferred, for conversion and selectivity, that the catalytic compositions of our invention reflect a range of about 20 to 35 weight percent iron, about 20 to 30 weight percent phosphorus component, and about 1 to 5 weight percent for the Group IIIA component, each component again expressive of the element itself, although not indicating that such component is necessarily present as the element itself.

A preferred group of catalytic compositions for conversion and selectivity, are aluminum or gallium Fe/P/O compositions.

A preferred group of catalysts at present, for selectivity and conversion, are Group IIIA metal-promoted calcined Fe/P/O compositions which contain phosphorus in an amount greater than that stoichiometrically required for simple iron phosphates. The amount of phosphorus present is in excess of the stoichiometric amount required for the phosphorus to react in the form of phosphate as $PO_4^{-3}$ ions with all of the iron in the iron reagent used to prepare the catalyst composition. The amount of such excess phosphorus should be in a range of about 1.01 to 5, more preferably about 1.01 to 2, times the stoichiometric amount for iron orthophosphate. These stoichiometric phosphorus contents vary, of course, according to the valence of the iron in the iron compound. Thus, for best results, more than 0.67 mole, preferably more than one mole, of phosphorus is present for each mole of iron.

Particularly effective, we have found, are Al- or Ga-promoted Fe/P/O catalyst compositions wherein the P is excess of the stoichiometric amount required as $PO_4^{-3}$ for the present according to the valence state of the iron to the extent of 1.01 to 5 times the stoichiometric amount.

CATALYST PREPARATION

The (I) iron component broadly can be derived from elemental iron or from any iron containing compounds as a class, including the presently preferred oxides or compounds convertible to the oxides on drying or calcining, such as the hydroxides or nitrates; as well as the halides including fluoride, chloride, bromide, or iodide; the halates including the bromates and other equivalent halates; carboxylates such as acetates, propionates, tartrates, and oxylates; the sulfates; the phosphates including complex phosphates; or the like; as well as mixtures or combinations thereof. The iron can be feric, ferrous, or combination ferroferric forms.

The (II) phosphorus component can be derived from elemental phosphorus or from any compound or mixtures of compounds of phosphorus, presently preferred being the oxides or compounds convertible thereto on drying or calcining.

The (III) Group IIIA metal component can be derived from any of the respective elements or from compounds or mixtures of compounds of boron, aluminum, gallium, indium, or thallium, such as boron oxide, aluminum oxide, gallium phosphate, indium phosphate, thallium phosphate, the nitrates, carboxylate, sulfates, or the like, presently preferred being the oxides or compounds convertible thereto on drying or calcining.

Double salts or compounds can be employed where desired, or compounds containing components from two or more groups can be utilized, such as aluminum phosphate, or iron phosphate, or the like, such that the resulting composition contains the desired components as we have described.

Relatively minor amounts of other element may be present as trace constituents in compounds or component-containing materials being employed, or present in a combined form not completely eliminated on drying and/or calcining. The presence of such is not unacceptable so long as not detrimental in a sufficient degree as to interfere in the effectiveness of our compositions as catalysts. For example, ammonium or alkali metal or alkaline earth metal hydroxides may be used in a preparation procedure such as precipitation. Small residual amounts of the alkali or alkaline earth metal hydroxides are not objectionable in the final compositions. Similarly, if iron sulfate or a Group IIIA metal sulfate is employed in the preparation, small residual amounts of combined sulfur can be tolerated. Halogen residues, on the other hand, presently are considered undesirable and should be minimized.

Our compositions and catalysts can be prepared by any method suitable which will result in the described compositions. Suitable methods include coprecipitation from aqueous or organic or combination solution-dispersions or suspensions, impregnation, dry mixing, or the like, alone or in various combinations. In general, any method can be utilized which provides effective amounts of the prescribed components in effective proportions. It is presently preferred that the final compositions, where they are to be employed as catalysts, have a sufficiently high surface area so as to permit most effective catalytic operation, such as about one square meter or more per gram.

One suitable and illustrative method of composition preparation involves admixing finely divided elements or one or more compounds such that the admixture contains the necessary components. The components can be admixed in the dry state, although adding sufficient water or other convenient diluent or slurry-forming liquid or suspension-forming material so as to make a workable slurry, and then intimately admixing usually is more convenient.

Where a slurry is prepared, the liquid components are removed such as by drying using vacuum or heat or combinations to form a dried composite, usually employing a temperature sufficient to volatilize the water or the diluents, such as from about 220 to 450° F., although lesser temperatures can be used under vacuum conditions.

The dry or otherwise dried composite is heated to an elevated temperature, which can be at any convenient suitable calcination range, such as about 900 to 1800° F., or more, more usually from about 1000 to 1400° F., over a time suitable or convenient, such as up to 24 hours more or less. The calcination step also provides activation of the compositions as catalysts. The activation-calcination step preferably includes exposure of the composite to a molecular oxygen-containing gas such as air, or oxygen diluted with some other component such as carbon dioxide, or steam, or other combination.

In preparation of one of the preferred catalysts of our invention, an iron/phosphorus/oxygen composition can be prepared by treating an iron oxide, or other compound such as iron hydroxide, any of the iron phosphates, or other suitable iron salt, with phosphoric acid. Alternatively, an iron compound can be dry mixed with such as phosphorous pentoxide, or the like, or, iron phosphates can be precipitated under conditions such that the precipitate contains the desired amount of phosphorus, preferably in excess of that required to combine with all of the iron in the form of orthophosphate. The resulting Fe/P/O composition, either before or after the calcination-activation step, can be impregnated conveniently with aqueous or nonaqueous solutions or dispersions of one or more Group IIIA metal compounds convertible to the oxide or substantially convertible to the oxide on calcination. For example, an excess-phosphorus Fe/P/O composite can be impregnated with an aqueous solution of aluminum nitrate. The impregnated composite is dried, and calcined in air. The base Fe/P/O composite can be initially calcined, then impregnated, and then activated by calcining. Or, the base composite can be simply a dry composite, the Group IIIA component added, and the entire composite then subjected to the activation-calcination step.

In an alternative method of catalyst preparation, solutions or dispersions of iron component- and Group IIIA metal component-containing compounds can be coprecipitated by the addition of an ammonium or an alkali metal or alkaline earth metal hydroxide. The precipitate obtained then is separated, washed, dried, and the resulting solid impregnated with a solution of a phosphorus containing compound such as phosphoric acid. Such a composite then is activated by calcination.

In preparation of low density porous catalyst compositions, a solution or dispersion containing compounds of iron, phosphorus, and Group IIIA metal component can be heated, with or without vacuum, until sufficient water has been removed that the admixture becomes, with continued application of heat, a hot viscous syrupy liquid. This substantially molecularly dehydrated admixture then subjected to a relatively rapid heating rate to raise the temperature to a relatively high range, such as to about 1000 to 1400° F. or more over an interval not exceeding about 4 hours, preferably not exceeding about 2 hours. Relative rapid heating to the calcination temperature range effects a foaming and expansion of the liquid mixture, and then ultimately solidification to a porous uniform mass having low apparent density. After reaching the calcination temperature, the mass is further heated in air or molecular oxygen containing gas at a calcination temperature for final activation as catalyst.

The compositions can be formed into any convenient shape or structure for utilization, depending on the particular purpose of use to which they may be put, type of reactor or contactor, and the like. The compositions can be prepared in the form of tablets, extrudates, finely divided powders, agglomerates, and the like, by various methods. For convenience in shaping, such particle-forming steps usually should be conducted prior to the calcination-activation step. Where desired, the composition subsequently to calcination-activation can be ground, and the ground composite compacted into form and density suitable for ultimate contacting and employment.

The compositions as catalysts can be prepared with or without a support. Where desired for strength, or for catalyst distribution or dilution in various types of reactors and for various feedstock contacting purposes, a variety of catalyst supports can be utilized including such as silica, boria, titania, zirconia, magnesia, singly, in admixture, or in combination such as silica-alumina and the like. When a support is utilized, the aforementioned weight ratios of one component to the other are exclusive of any such support material.

DEHYDROGENATION FEEDSTOCKS

Organic feedstocks for which our compositions can be employed as catalysts in oxidative dehydrogenation processes are those feedstreams or feedstocks containing one or more dehydrogenatable organic compounds alone or in admixture, or in diluted form with nondehydrogenatable material such as steam, nitrogen, and the like.

Dehydrogenatable organic compounds can be characterized as containing at least one

grouping. Compounds to be so dehydrogenated typically contain in the range of 2 to 12 carbon atoms per molecule. It is feasible to dehydrogenate compounds of a dehydrogenatable character containing a greater number of carbon atoms, although such are not often readily commercially available. More specifically, the upper carbon limitation mentioned does not indicate limitation on the effectiveness of our compositions where employed as catalysts, nor of processes employing our compositions, but only refers to suggested more available feedstocks. Compounds to be dehydrogenated can be of branched or unbranched structure.

Particularly suitable for processes employing our compositions as catalysts are the hydrocarbons, including cyclic and acyclic as well, more particularly the acyclic. Particularly desired for dehydrogenatable feedstocks employing our compositions as catalysts are the dehydrogenatable acyclic monoolefins such as 1-olefins or 2-olefins, although other monoolefins also can be successfully dehydrogenated to a higher degree of unsaturation. Dehydrogenatable alkenes can be converted, particularly those having from 3 to 12, presently preferably 4 to 6, carbon atoms per molecule, and the cycloalkenes containing from 4 to 10, preferably 4 to 6, carbon atoms per molecule, which can be converted to the corresponding alkadienes and cycloalkadienes.

In addition, alkylpyridines and alkyl aromatic compounds containing from 1 to 4, preferably 1 to 2, alkyl groups per molecule wherein the alkyl groups themselves contain from 1 to 6, preferably 2 to 6, carbon atoms per group and including at least one alkyl group having a minimum of 2 carbon atoms, can be converted to the corresponding alkenyl-substituted pyridines and alkenyl-substituted aromatic compounds.

Feedstocks utilized can be relatively pure feedstocks, i.e., a single compound; or can be employed as mixed feedstocks available from various refinery streams and containing a variety of components dehydrogenatable or some merely diluent in the sense of not being dehydrogenatable.

The conversions of isoamylenes to isoprene, butenes to butadiene, ethylbenzene to styrene, and 2-methyl-5-ethylpyridine to 2-methyl-5-vinylpyridine, presently are considered most advantageous. Representative feedstocks or feedstock components include ethane, 2,4-dimethyloctane, 2-methylbutene-1, hexene-2, octene-1, 3-methylnonene-4, dodecene-1, propylene, n-butenes, n-pentenes, isopentenes, cyclobutene, cyclopentene, cyclohexene, 3-isobutyl-cyclopentene, ethylbenzene, propylbenzene, isobutylbenzene, 1-methyl-2-propylbenzene, 1-butyl-3-hexylbenzene, ethylpyridine, 2-methyl-5-ethyl pyridine, 2,3,4-triethylmethyl-5-ethyl pyridine, 2ethyl-5-hexyl pyridine, and the like.

In the course of oxidative dehydrogenation processes some amounts, generally small amounts, of oxygenated products also may be formed. These products may include such as furan, aldehydes such as acetaldehyde from the conversion of butenes, and the like. Other compounds such as furfural, or even acids such as acetic acid, may be obtained. Carbon oxides and water also may be formed either by chemical reactions, or, in the case of water also by condensation of the steam during recovery of the products.

In another embodiment of oxidative processes employing our compositions as catalysts, dehydrogenatable feedstocks of the cyclic and acyclic alkadienes of 4 to 12 carbon atoms, per molecule although compounds of greater number of carbon atoms are useful, preferably of 4 to 6 carbon atoms, can be employed to produce a variety of oxygenated products such as ethers, aldehydes, acids, and the like. The diene feedstocks, such as butadiene, octadiene, and the like, can correspond to any of the monoolefin compounds already exemplified, simply adding the further double bond, without needlessly repeating a list of exemplary compounds.

DEHYDROGENATION CONDITIONS

In a dehydrogenation process, the feedstock, together with a molecular-oxygen containing gas, optionally preferably further with steam, is form into admixture, preferably preheated, and then contacted with our compositions as catalysts.

Any contacting method or reactor suitable for the oxidative dehydrogenation arts can be employed, such as the presently preferred fixed contacting catalyst beds, as a single bed, as a graded series of beds of differing degree of catalyst activity or of contacting temperatures, or by any other contacting method or approach such as fluidized beds, and the like.

Hydrocarbon feedstocks to be dehydrogenated according to the process of our invention can be contacted at contacting temperatures over a broad range, utilizing any contacting pressures and feed rates, oxygen:hydrocarbon ratios, hydrocarbon:steam ratios, employed in the dehydrogenation arts and suitable for the degree or extent of conversion desired within contacting times to be employed.

Suggested contacting conditions include temperatures in the range of about 800° to 1300° F., presently preferably 900° to 1100° F.; contacting pressures of about 0.05 to 250 psia, presently preferably about 0.1 to 25 psia; oxygen:feed ratios of about 0.1:1 to 3:1, presently preferably about 0.5:1 to 2:1, volumes of oxygen per volume of feed; steam:feed ratios of about 0.1:1 to 100:1, presently preferably about 5:1 to 20:1, volumes of steam per volume of feed; gaseous hourly space velocity GHSV of about 50 to 5000, presently preferably about 100 to 2500, volumes of organic feed vapor per volume of catalyst per hour.

The use of steam frequently is beneficial in dehydrogenation processes for heat transfer purposes to assist in removing heat of reaction. Where steam is so employed, a steam:hydrocarbon ratio of up to about 100:1 or more can be utilized, although further dilutions presently appear unnecessary and wasteful of the steam.

Effluent from the reaction zone or zones can be subjected to any suitable separation method so as to isolate and recover desired product or products, to separate unconverted or partially converted feed or components for recycle to the contacting zone or for other use in the modern integrated chemical refinery or petrochemical processing operation which more and more frequently is being termed a petrocomplexity.

Our compositions, employed under appropriate conditions as catalysts, have a long active life and seldom need, if ever, to undergo regeneration. However, should regeneration become indicated or is desired, according to operational controls, or because of inactivation possibly attributable to minor amounts of poisons, such as in the feedstocks, or introduced inadvertently or for other causes, our catalyst compositions can be readily regenerated. Regeneration can be accomplished by ceasing the flow of feedstock, continuing the flow of molecular oxygen-containing gas, preferably also of steam in order to maintain suitable temperatures, and otherwise maintaining operating conditions of temperature and the like for a sufficient time to restore substantial activity to the catalyst compositions.

Over prolonged intervals of service, in some instances, some of the phosphorus may tend to dissipate from the catalyst compositions. Consequently, to maintain such catalyst at a suitably high level of activity, a small effective quantity of a phosphorus-containing compound can be intermittently or continuously introduced into the reaction zone, conveniently during operational intervals. The level of phosphorus addition can correspond to the level of phosphorus loss, which latter can be readily determined by analysis of reactor effluent, particularly analysis of steam condensate. Any suitable phosphorus compound can be employed such as any of the phosphoric acids, phosphorus oxides such as phosphorus pentoxide, as well as organophosphorus compounds such as the organo-substituted phosphines and the like can be used.

EXAMPLE

The following data serve to illustrate the use of our compositions as catalysts. Particular components, species, conditions employed, are intended to be illustrative of our invention and not limitative of the reasonable and proper scope thereof.

Al/Fe/P/O Catalyst A: 150 ml of 1 molar $Fe(NO_3)_3$ were mixed with 20 ml of $H_3PO_4$ (85 percent), and 6 g of $Al(NO_3)_3 \cdot 9H_2O$. The resulting solution was evaporated by heating with stirring until it became a sticky syrup. The syrup was transferred to a furnace and heated up to 1200° F. over a 2-hour period, and then calcined at 1200° F. for 4 additional hours. The resulting composition was ground and screened to 20 to 28 mesh size. The catalyst contained 3 percent Al, 25 percent Fe, and 27 percent P, by weight.

Fe/P/O Catalyst B: For purposes of comparison, a similar but Al-free Fe/P/O catalyst was prepared containing 23 percent Fe and 27 percent P, by weight.

Ga/Fe/P/O Catalyst C: 9 g of $Ga(NO_3)_3 \cdot 9H_2O$ were mixed with 7 ml of $H_3PO_4$ (85 percent) and diluted to 45 ml with water. The resulting solution was mixed with 30 g of $Fe_3(PO_4)_2$. The mixture was dried and calcined 4 hours at 1200° F. The catalyst contained 4.8 percent Ga, 30 percent Fe, and 22 percent P, by weight.

Fe/P/O Catalyst D: For purposes of comparison, a similar but Ga-free Fe/P/O catalyst was prepared containing 30 percent Fe and 22 percent P, by weight.

The catalysts prepared as described above were tested for activity in an oxidative dehydrogenation conversion of 2-methylbutene-2 (2-MB-2) to isoprene. A mixture of 2-methylbutene-2, steam, and air was passed through a fixed bed of each of the catalysts. The results, as well as the essential reaction conditions, are shown in Table I below.

TABLE I

Oxidative Dehydrogenation of 2-Methylbutene-2 to Isoprene

| Catalyst | Conv.[a] | Modivity, %[b] | Yield[c] | 2-MB-2 | GHSV Air | Stream |
|---|---|---|---|---|---|---|
| A. Al/Fe/P/O | 62 | 90 | 56 | 400 | 3,000 | 10,000 |
| B. Fe/P/O | 76 | 71 | 54 | 400 | 3,000 | 10,000 |
| C. Ga/Fe/P/O | 67 | 87 | 58 | 200 | 1,000 | 5,000 |
| D. Fe/P/O | 54 | 79 | 43 | 200 | 1,000 | 5,000 |

[a]Conversion expressed as moles of isoamylenes consumed per 100 moles 2-MB-2 fed, sampled after 36 hours on stream at 1050° F. and atmospheric pressure.
[b]Modivity is a modified selectivity based on analysis of gas phase products which include carbon oxides, cracked products, isoprene, and isoamylenes.
[c]Yield expressed as moles of isoprene per 100 moles 2-MB-2 converted.

The data in Table I above illustrate the beneficial results obtained by incorporating a Group IIIA metal, here Ga or Al, into a Fe/P/O oxidative dehydrogenation catalyst. Both the selectivity to and the yield of desired product were increased.

Reasonable variations and modifications of our invention are possible while still within the scope of our disclosure, and without departing from the reasonable scope and spirit thereof as detailed in our specification as well as the here-appended claims.

What is claimed is:

1. A process of oxidative dehydrogenation of at least one dehydrogenatable organic compound containing at least one 1. [A process] which comprises contacting said dehydrogenatable organic compound under oxidative dehydrogenation conditions with molecular oxygen and a catalyst consisting essentially of (I) about 15 to 45 weight percent iron, (II) about 15 to 40 weight percent phosphorus, and (III) about 0.1 to 10 weight percent of a promoter which is boron, aluminum, indium, or thallium, and (IV) oxygen, wherein the weight percents are based on the total composition exclusive of support, if any.

2. The oxidative dehydrogenation process according to claim 1 wherein said (I) iron represents about 20 to 35 weight percent, said (II) phosphorus about 20 to 30 weight percent, and said (III) promoter about 1 to 5 weight percent.

3. A process of oxidative dehydrogenation of at least one dehydrogenatable organic compound containing at least one

grouping which comprises contacting said dehydrogenatable organic compound under oxidative dehydrogenation conditions with molecular oxygen and a catalyst composition consisting essentially of (I) iron, (II) phosphorus, (III) a promoter which is boron, aluminum, indium, or thallium, and (IV) oxygen, optionally with a support wherein the weight percent of each of said (I), said (II), and said (III), calculated at the element, is in a ratio of each to the other effective for said oxidative dehydrogenation, and wherein said phosphorus is present in an amount from about 1.01 to 5 times the stoichiometric amount required by iron orthophosphate.

4. The oxidative dehydrogenation process according to claim 3 wherein said (I) represents about 15 to 45 weight percent, said (II) about 15 to 40 weight percent, and said (III) about 0.1 to 10 weight percent.

5. The oxidative dehydrogenation process according to claim 4 wherein said (I) represents about 20 to 35 weight percent, said (II) about 20 to 30 weight percent, and said (III) about 1 to 5 weight percent.

6. The oxidative dehydrogenation process according to claim 5 wherein said catalyst composition is Al/Fe/P/O.

7. The oxidative dehydrogenation process according to claim 5 wherein said catalyst composition is B/Fe/P/O.

8. The oxidative dehydrogenation process according to claim 5 wherein said catalyst composition is In/Fe/P/O.

9. The oxidative dehydrogenation process according to claim 5 wherein said catalyst composition is Tl/Fe/P/O.

10. The oxidative dehydrogenation process according to claim 2 wherein said (III) is boron.

11. The oxidative dehydrogenation process according to claim 2 wherein said (III) is aluminum.

12. The oxidative dehydrogenation process according to claim 2 wherein said (III) is indium.

13. The oxidative dehydrogenation process according to claim 2 wherein said (III) is thallium.

14. The oxidative dehydrogenation process according to claim 1 wherein said catalyst composition further employs said support, and said support is one or more of silica, alumina, boria, titania, zirconia, magnesia, mixtures or combinations thereof.

15. A process of oxidative dehydrogenation of at least one dehydrogenatable organic compound containing at least one

grouping wherein said dehydrogenatable organic compound is contacted under oxidative dehydrogenation conditions with molecular oxygen and a catalyst, wherein said catalyst composition consists essentially exclusive of support, if any of (I) about 15 to 45 weight percent iron, (II) about 15 to 40 weight percent phosphorus, (III) about 0.1 to 10 weight percent of a promoter which is at least one Group IIIA component and which is boron, aluminum, indium, or thallium, and (IV) oxygen in a combined form with one or more of said 1, 2 and 3, wherein the weight percent of each of said 1, 2, 3, and 4 is in a ratio of each to the other sufficient to provide catalytic effectiveness, and wherein said catalyst composition is prepared by the process which comprises the steps of admixing compounds of iron, phosphorus, and of a said Group IIIA component in water, heating until sufficient water has been removed such that the resulting admixture becomes a viscous syrupy liquid, thereafter molecularly dehydrating the viscous syrupy liquid at a relatively rapid heating rate sufficient to result in a foamed expanded porous mass, and calcining said porous mass in the presence of a molecular oxygen-containing gas.

16. The oxidative dehydrogenation process according to claim 15 wherein said Group IIIA component is aluminum.

17. A process according to claim 1 wherein said dehydrogenatable organic compound comprises an acyclic monoolefin of at least 3 carbon atoms per molecule, cyclic alkenes of at least 4 carbon atoms per molecule, alkylpyridines or alkylaromatics such that at least 1 alkyl group has at least 2 carbon atoms, and cyclic or acyclic alkadienes of at least 4 carbon atoms per molecule.

18. The process according to claim 17 wherein said acyclic monoolefin contains 3 to 12 carbon atoms per molecule, said cyclic alkenes contain 4 to 10 carbon atoms per molecule, said alkylpyridines or alkylaromatics contain 1 to 4 alkyl groups per molecule, and said cyclic or acyclic alkadienes contain 4 to 12 carbon atoms per molecule.

19. The process according to claim 1 wherein said oxidative dehydrogenation conditions include the employment of steam, and wherein said oxidative dehydrogenation conditions include contacting temperature of about 800° to 1300° F.; contacting pressure of about 0.05 to 250 psia; oxygen:feed ratio of about 0.1:1 to 3:1 volumes of oxygen per volume of feed; steam:feed ratio of about 0.1:1 to 100:1 volumes of steam per volume of feed; and a GHSV of about 50 to 5000 volumes of organic feed vapor per volume of catalyst per hour.

20. The process according to claim 3 further employing a feed of small effective amount of at least one phosphorus-containing compound sufficient to substantially maintain catalyst activity.

21. The process according to claim 15 wherein said (III) is aluminum and said dehydrogenatable hydrocarbon is 2-methylbutene-2.

22. A dehydrogenation process according to claim 19 wherein said catalyst composition is prepared by impregnating an Fe/P/O composition with a promoting amount of a solution or dispersion of a boron or aluminum compound substantially convertible to the oxide on calcination, and calcining said impregnated composite in the presence of a molecular oxygen-containing gas.

23. A dehydrogenation process according to claim 19 wherein said catalyst composition is prepared by steps comprising preparing solutions or dispersions of an iron compound and an aluminum or boron-containing compound, coprecipitating by the addition of an ammonium or alkali metal or alkaline earth metal hydroxide, drying the precipitate so obtained, impregnating the resulting solid with a solution of a phosphorus-containing compound, and calcining the impregnated composition in the presence of a molecular oxygen-containing gas.

24. A dehydrogenation process according to claim 19 wherein said catalyst composition is prepared by steps comprising admixing solutions containing compounds of iron, phosphorus, and of boron or aluminum, heating until sufficient water has been removed that the admixture becomes a viscous syrupy liquid, thereafter molecularly dehydrating at a relatively rapid heating rate sufficient to provide a foamed expanded porous mass, and calcining said porous mass in the presence of a molecular oxygen-containing gas.

25. An oxidative dehydrogenation process employing a catalyst composition consisting essentially of iron/phosphorus/Group IIIA component/oxygen wherein a dehydrogenatable organic compound containing at least one

grouping is contacted with oxygen and said catalyst composition under oxidative dehydrogenation conditions, thereby converting said dehydrogenatable organic compound to one or more compounds having a greater degree of unsaturation, wherein said catalyst composition is prepared by the steps which comprise heating an aqueous admixture containing compounds of iron, phosphorus, and of a Group IIIA compound until sufficient water has been removed such that the resulting admixture is a viscous syrupy liquid, thereafter molecularly dehydrating the viscous syrupy liquid at a relatively rapid heating rate sufficient to result in a foamed expanded porous mass, then calcining said porous mass in the presence of a molecular oxygen-containing gas, wherein said Group IIIA component is selected from the group consisting of aluminum, boron, indium, and thallium, and wherein said dehydrogenatable organic compound comprises an acyclic monoolefin of at least 3 carbon atoms per molecule, cyclic alkene of at least 4 carbon atoms per molecule, alkylpyridine or alkylaromatic such that at least one alkyl group has at least 2 carbon atoms, or cyclic or acyclic alkadienes of at least 4 carbon atoms per molecule.

26. A process according to claim 25 wherein said oxidative dehydrogenation conditions include employment of steam, said conditions include contacting temperatures of about 800° to 1300° F., pressures of about 0.05 to 250 psia, oxygen:feed ratios of about 0.1:1 to 3:1 volumes of oxygen per volume of feed, steam:feed ratios of about 0.1:1 to 100:1 volumes of steam per volume of feed, and a GHSV of about 50 to 5000 volumes of organic feed vapor per volume of said catalyst per hour, and said process further employs a feed of a small effective amount of at least one phosphorus-containing compound sufficient to substantially maintain catalyst activity.

27. The process according to claim 26 wherein said (III) is aluminum, and said dehydrogenatable organic hydrocarbon is 2-methylbutene-2.

* * * * *